United States Patent [19]

Umezawa et al.

[11] 4,179,573
[45] Dec. 18, 1979

[54] (2S,3R)-3-AMINO-2-HYDROXY-4-PHENYL-BUTANOIC ACID

[75] Inventors: Hamao Umezawa, Tokyo; Takaaki Aoyagi, Fujisawa; Tomio Takeuchi, Tokyo; Masa Hamada, Hoya; Yoshiro Okami, Tokyo, all of Japan

[73] Assignee: Zaidan Hojin Biseibutsu Kagaku Kenkyu Kai, Tokyo, Japan

[21] Appl. No.: 825,997

[22] Filed: Aug. 19, 1977

Related U.S. Application Data

[60] Division of Ser. No. 690,457, May 27, 1976, Pat. No. 4,052,449, which is a continuation-in-part of Ser. No. 591,924, Jun. 30, 1975, abandoned.

[30] Foreign Application Priority Data

Jul. 1, 1974 [JP] Japan .................................. 49-75090

[51] Int. Cl.² ............................................ C07C 101/72
[52] U.S. Cl. .................................................. 562/444
[58] Field of Search ......................... 260/519; 562/444

[56] References Cited

PUBLICATIONS

Knoop et al., [Z. Physiol Chem., vol. 239, 30–46 (1936)], Chem. Abst., vol. 30; #2583⁵.
Aries, Chem. Abst, vol. 83, #131311 (1975).

Primary Examiner—James H. Reamer
Attorney, Agent, or Firm—Herbert W. Taylor, Jr.

[57] ABSTRACT

This invention provides the amino acid (2S,3R)-3-amino-2-hydroxy-4-phenylbutanoic acid which is prepared by hydrolysis of bestatin. Bestatin is a chemical which inhibits aminopeptidase B, leucine aminopeptidase and bleomycin hydrolase, enhances the antitumor effect of bleomycin, has the chemical name [(2S,3R)-3-amino-2-hydroxy-4-phenylbutanoyl]-L-leucine, has the following structure

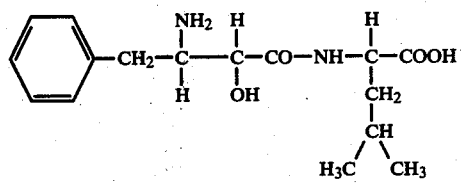

and is prepared by cultivating a strain of streptomyces which produces bestatin in a nutrient medium under aerobic conditions until substantial activity inhibitory to aminopeptidase B is imparted to said cultured medium and then recovering said bestatin from said cultured medium. A preferred strain is *Streptomyces olivoreticuli* FERM-P No. 2590 (A.T.C.C. 31159).

1 Claim, No Drawings

(2S,3R)-3-AMINO-2-HYDROXY-4-PHENYL-BUTANOIC ACID

CROSS REFERENCE TO RELATED APPLICATIONS

This application is a division of our prior, copending application Ser. No. 690,457, filed May 27, 1976 and issued Oct. 4, 1977 as U.S. Pat. No. 4,052,499 which was in turn a continuation-in-part of prior copending application Ser. No. 591,924 filed June 30, 1975 now abandoned.

BACKGROUND OF THE INVENTION (1) Field of the Invention

This invention relates to an inhibitor, called bestatin, of aminopeptidase B, leucine aminopeptidase and bleomycin hydrolase which is produced by aerobic cultivation of streptomyces and includes processes for its production by fermentation and for its extraction.

(2) Description of the Prior Art

Bestatin is a substance found and isolated from culture broth of a streptomyces and has interesting biological and physiological activities. Namely, bestatin has substantially no antibacterial activity, but exhibits a weak inhibition of growth of mammalian cells including cancer cells and a strong inhibition of aminopeptidase B, leucine aminopeptidase and bleomycin hydrolase. Based on inhibition of bleomycin hydrolase, it exhibits a strong synergistic activity with bleomycin in inhibiting tumors. Therefore, bestatin is very important not only in treatment of squamous cell carcinoma by bleomycin, but also in analysis of biological functions and disease processes.

SUMMARY OF THE INVENTION

This invention relates to a new and useful microbial product named bestatin which inhibits aminopeptidase B, leucine aminopeptidase and bleomycin hydrolase. It also relates to processes for its production by fermentation and methods of its recovery and purification. This invention embraces this enzyme inhibitor and its salts as crude concentrates, crude solids, as purified solids and pure forms. This substance and its salts are effective in inhibiting aminopeptidase B, leucine aminopeptidase and bleomycin hydrolase, in weakly inhibiting mammalian cancer cells and in increasing bleomycin activity against squamous cell carcinoma. Bestatin and its salts have low toxicity and are useful for the treatment of squamous cell carcinoma when combined to bleomycin.

There is now provided, according to the present invention, an anti-aminopeptidase B compound (and its salts), denominated bestatin, which are effective in inhibiting hydrolysis action of aminopeptidase B, leucine aminopeptidase and bleomycin hydrolase and in increasing antitumor activity of bleomycin, said compound being soluble in water, acetic acid, pyridine, dimethylsulfoxide, methanol and ethanol, slightly soluble in propanol and butanol, practically insoluble in ethyl acetate, butyl acetate, ethyl ether, hexane, petroleum ether, benzene and chloroform, melting at 233°–236° C., exhibiting levoration of $[\alpha]_D^{22} = -30.6°$ (c=0.861, methanol) and $[\alpha]_D^{20} = -15.5°$ (c=1.0, 1 N HCl), exhibiting strong end absorption with maxima at 241.5 nm ($E_{1\ cm}^{1\%} = 3.8$), 248 nm ($E_{1\ cm}^{1\%} = 4.0$); 253 nm ($E_{1\ cm}^{1\%} = 5.0$); 258 nm ($E_{1\ cm}^{1\%} = 6.0$), 264.5 nm ($E_{1\ cm}^{1\%} = 4.6$) and 268 nm ($E_{1\ cm}^{1\%} = 2.7$), giving positive Rydon-Smith and ninhydrin reactions and negative Ehrlich and Sakaguchi reactions, exhibiting the following absorption maxima in the infrared region of the spectrum when pelleted with potassium bromide: 3400, 3300, 3200, 2920, 2850, 1685, 1635, 1530, 1400, 1315, 1265, 1245, 1175, 1125, 1100, 850, 735, 700 cm$^{-1}$, having the formula $C_{16}H_{24}N_2O_4$ which is shown by the mass spectrum and elemental analysis (found: C 60.86% H 7.79%, N 8.61%), yielding L-leucine and a new amino acid [(2S,3R)-3-amino-2-hydroxy-4-phenylbutyric acid] which structure is shown by X-ray crystal analysis of the hydrobromide of its methyl ester, yielding acid salts which are more soluble in water than bestatin, exhibiting inhibition of aminopeptidase B, leucine aminopeptidase and bleomycin hydrolase and having the following structure shown by nmr, structures of hydrolysis products and chemical systhesis:

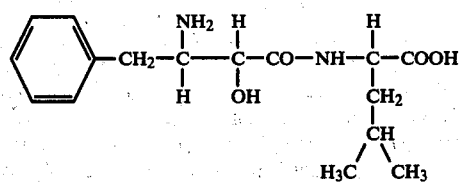

The chemical name for bestatin is [(2S,3R)-3-amino-2-hydroxy-4-phenylbutanoyl]-L-leucine and it may also be named N-[(2S,3R)-3-amino-2-hydroxy-4-phenylbutanoyl]-2S-leucine.

There are included within the scope of the present invention the amphoteric bestatin and its salts. Acid salts of bestatin can be easily obtained by addition of equimolar acid and the salts such as the hydrochloride, acetate, etc. are more soluble in water than bestatin. Basic salts are formed by the addition of alkali such as sodium or potassium hydroxide. The pharmaceutically acceptable salts of the substances of the present invention include nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)alkyl-piperidine, e.g. N-ethylpiperidine, and other amines which have been used to form salts with benzylpenicillin.

There is further provided, according to the present invention, the processes for production of bestatin which comprise cultivating a bestatin-producing strain of streptomyces in an aqueous solution containing carbon sources and nitrogen sources under aerobic conditions until a substantial amount of bestatin is accumulated in said solution and extracting and isolating bestatin therefrom.

The present inventors have thought that microorganisms produce protease inhibitors, and after discoveries of leupeptin inhibiting trypsin, chymostatin inhibiting chymotrypsin, pepstatin inhibiting acid proteases and phosphoramidon inhibiting metalloendopeptidases, by the continuation of the study, bestatin was discovered in culture filtrates of a streptomyces. Moreover, bestatin was found to inhibit enzymatic inactivation of bleomycin in mammalian cells and to increase the bleomycin therapeutic effect on squamous cell carcinoma. As described by H. Umezawa, one of the inventors, in his book "Enzyme Inhibitors of Microbial Origin" published by the University of Tokyo Press, Bunkyo-ku, Tokyo in 1972, protease inhibitors are obtained from various species of streptomyces. This is the same in bestatin. In this invention, characteristics of a typical bestatin-producing strain are described. The description in brackets [ ] follows the color standard shown in Color Harmony Manual of Container Corporation of America.

The Characteristics of the strain MD976-C7:

The strain was isolated from a soil sample collected at Kaitamura-Nishino, Kisogun, Nagano. It was deposited in Kogyo Gijutsuin Hakko Kenkyusho on May 18 of 1974 and the deposit number is 2590. This strain is deposited in American Type Culture Collection and the number ATCC 31159 was given, and therefore it is now available for scholars. Microscopically, substrate mycelia are well branched and extend aerial hypae. On aerial hypae, spirals are not observed but whorls are observed. Surface of spores is smooth.

The characters on various media are as follows:

(1) On sucrose nitrate agar medium (cultured at 27° C.): growth is poor and colorless, and white [a, White] aerial mycelium develops slightly; no soluble pigment.

(2) On glucose asparagine agar medium (cultivated at 27° C.): growth is pale yellowish brown [1½ ic, Lt Antique Gold], and white [a, White] to grayish white [b, Oyster White] aerial mycelium develops; no soluble pigment.

(3) On glycerol-asparagine agar medium (ISP-5, cultured at 27° C.): growth is pale yellowish brown [1½ ic, Lt Antique Gold], and around the growth white [a, White] to grayish white [b, Oyster White] aerial mycelium develops; no soluble pigment.

(4) Inorganic salts-starch agar medium (ISP-4, cultured at 27° C.): growth is pale yellowish brown [1½ ic, Lt Antique Gold] to yellowish brown [2 lc, Gold], and on the growth light brownish gray [4 ec, Bisque Lt Rose Beige] aerial mycelium develops; no soluble pigment.

(5) On tyrosine agar medium (ISP-7, cultured at 27° C.): growth is pale yellow [1½ ia, Sunlight Yellow, Daffodil, Forsythia, Jonquil] to pale yellowish brown [1½ ic, Lt Antique Gold], and on the growth grayish white [b, Oyster White] aerial mycelium develops; no soluble pigment.

(6) On peptone-meat extract agar medium (cultured at 27° C.): growth is pale yellowish brown [1½, Lt Antique White], and around the colony grayish white [b, Oyster White] aerial mycelium develops; pale yellowish brown soluble pigment is produced slightly.

(7) On yeast extract-malt extract agar medium (ISP-2, cultured at 27° C.): growth is dull yellow [2 lc, Gold] to yellowish brown [2 pg, Mustard Gold], and on the growth grayish white [b, Oyster White] to light brownish gray [4 ec, Bisque, Lt Rose Beige] aerial mycelium develops; pale yellow brown soluble pigment slightly.

(8) On oatmeal agar medium (ISP-3, cultured at 27° C.): growth is pale yellow [1½ ia, Sunlight Yellow, Daffodil, Forsythia, Jonquil], and on the growth grayish white [b, Oyster White] aerial mycelium develops slightly; no soluble pigment.

(9) On calcium malate agar medium (cultured at 27° C.): growth is colorless, and on the growth white [a, White] aerial mycelium develops; no soluble pigment.

(10) On glucose peptone geratin agar stab: growth is yellowish brown [2 lc, Gold], and on the growth light brownish gray [4 ec, Bisque, Lt Rose Beige] aerial mycelium develops; brownish black soluble pigment is produced.

(11) On milk medium (cultured at 27° C.): growth is pale yellow [1½ ia, Sunlight Yellow, Daffodil, Forsythia, Jonquil] to pale yellowish brown [1½ ic, Lt Antique Gold]; no aerial mycelium; pale yellowish brown pigment is produced.

(12) On peptone-yeast extract iron agar medium (ISP-6, cultured at 27° C.): growth is dark brownish gray [3 li, Beaver], and on the growth grayish white [b, Oyster White] aerial mycelium develops slightly; brownish black pigment is produced.

Physiological and biochemical properties:

(1) Growth temperature: it grew on maltose yeast extract agar medium in the range of from 15° C. to 37° C. and the optimum temperature was 22°–32° C.

(2) Liquefaction of gelatin (tested on glucose peptone gelatin medium at 20° C.); no liquefaction of gelatin.

(3) Hydrolysis of starch (tested on inorganic salts-starch agar medium-ISP-4 at 27° C.): hydrolysis was observed after 4 days and the hydrolytic strength was medium.

(4) Coagulation and peptonization of milk (tested at 37° C.): complete coagulation occurred after 3 days and peptonization was observed thereafter. The strength was medium.

(5) Production of melanoid pigment (tested on tryptone-yeast extract broth (ISP-1), peptone-yeast extract iron agar medium (ISP-6), tyrosine agar medium (ISP-7) at 27° C.): melanoid pigment was produced in these media except tyrosine agar medium.

(6) Utilization of carbon sources (tested on Pridham Gottlieb medium): glucose and fructose were utilized, yielding good growth; L-arabinose, D-xylose, sucrose, L-rhamnose, raffinose, and D-mannitol were not utilized. Inositol utilization was doubtful.

(7) Hydrolysis of calcium malate (tested on calcium malate agar medium cultured at 27° C.): no hydrolysis.

(8) Nitrate reduction (tested on 1.0% nitrate peptone water at 27° C.): negative reduction.

The characteristics described above can be summarized as follows: the strain MD976-C7 belongs to streptomyces which forms whorls when grown on sucrose nitrate agar medium and glucose-added Pridham Gottlieb medium, but not spirals; its spore surface is smooth; growth on various media is pale yellow, pale yellowish brown or dull brown; and aerial mycelium on the growth is white, light brownish gray or grayish white; pale yellowish brown pigment is produced occasionally; melanoid pigment is produced in organic nitrogen media but not in tyrosine agar; a weak proteolytic activity; medium grade of starch hydrolysis. If these characters are compared with those of known species, then, the strain MD976-C7 is most closely related to *Streptomyces olivoreticuli* which Arai et al described in Antibiotics and Chemotherapy 7, 435–442, 1957. Description of this species, the ISP Type Culture-5105 and the strain MD976-C7 were directly compared, and it was confirmed that there is nothing of significant difference between the strain MD976-C7 and *Streptomyces olivoreticuli*. Thus, this strain was classified to this species.

Since inhibitors of all proteases are produced by various species of streptomyces and the production is not limited to a single species, in this invention, instead of names of the above species, bestatin-producing streptomyces is used for description.

Method of testing the activity of bestatin inhibiting aminopeptidase B:

The method described by V. K. Hopusu, K. K. Makinen, G. G. Glenner in Archives of Biochemistry and Biophysics 114, 557, 1966 was modified. To the mixture of 0.3 ml of 1 mM arginine $\beta$-naphthylamide and 1.0 ml of 0.1 M Tris hydrochloride buffer (pH 7.0), 0.7 ml of distilled water with or without a test material is added and warmed at 37° C. for 3 minutes. The reaction is started by addition of 0.2 ml of aminopeptidase B solution which is prepared by Sephadex 100 chromatography as described by Hopusu et al. After 30 minutes at 37° C., 0.6 ml of 1.0 M acetate buffer (pH 4.2) containing diazonium salt of o-aminoazotoluene at 1.0 mg/ml and Tween 20 at 10% is added. Fifteen minutes at room temperature thereafter, absorbance (a) at 530 nm is measured by spectrophotometer. As the control, by similar means, the absorbance (b) after the reaction in the absence of bestatin is measured. The inhibition percent is calculated as follows: $(b-a)/b \times 100$. The 50% inhibition dose ($ID_{50}$) of bestatin was 0.1 $\mu$g.

A bestatin-producing strain when grown under suitable conditions produces bestatin. For production of bestatin cultivation on a solid medium is possible, but for production of large quantities cultivation in a liquid medium is preferred. Any fermentation temperature can be employed to produce bestatin within the range in which bestatin-producing organisms can grow, although 25°-35° C. is preferred. Media containing known nutritional sources for actinomycetes are useful for production of bestatin. For example, commercial products such as peptone, meast extract, yeast extract, corn steep liquor, cotton seed flour, soybean flour, N-Z amine, casein, sodium nitrate, ammonium nitrate, ammonium sulfate and other nitrogenous materials such as wheat bran, rice bran, fish meal etc are useful for nitrogen source. The commercially available products such as lactose, glycerol, sucrose, starch, glucose, maltose, molasses and other carbohydrates or fats in pure or crude state are useful as the carbon source. Sodium chloride, sodium or potassium phosphate, calcium carbonate or magnesium ion can also be added. Any material which have been known for cultivation of actinomycetes are useful.

The fermentation is continued until bestatin is substantially accumulated. For example, the MD976-C7 strain was inoculated to media containing NaCl 0.3%, $MgSO_4 \cdot 7H_2O$ 0.1%, $K_2HPO_4$ 0.1%, metal solution 0.1 ml/100 ml, organic nitrogen source and carbon source. The nitrogen sources added to media were as follows: meat extract 0.75% and peptone 0.75%; N-Z amine 1.0% and yeast extract 0.2%; soybean meal 1.5%. The carbon sources added to the media were as follows: glycerol 2.0%; lactose 2.0%; glucose 1.0% and lactose 1.0%. The metal solution consisted of $CuSO_4 \cdot 5H_2O$ 700 mg, $FeSO_4 \cdot 7H_2O$ 100 mg, $MnCl_2 \cdot 4H_2O$ 800 mg, $ZnSO_4 \cdot 7H_2O$ 200 mg in 100 ml of distilled water. Shake flasks of 500 ml volume were used and 100 ml of each medium was placed. It was shake-cultured at 27°-29° C. on a reciprocating shaking machine (amplitude 8 cm, 200 strokes/minute). Bestatin production was recognized after 2 days of the shaking culture and the maximum yield was obtained on 2-6 day of the culture. Among nitrogen sources used, the better yield was obtained in media containing meat extract 0.75% and peptone 0.75%, N-Z amine 1.0% and yeast extract 0.2% or soybean meal 1.5% than in the medium containing corn steep liquor 1.5%. Bestatin was produced in any media containing glycerol, lactose, or glucose and the yield was not significantly different in media containing one of these carbon sources. During fermentation, there was no decrease of bestatin in the media, suggesting its stability.

For production of bestatin by fermentation, the ordinary methods used for antibiotics can be employed. For instance, 100-150 liters of a medium were placed in a stainless steel fermenter of 200 liters volume, and sterilized, bestatin-producing organisms were inoculated, and fermentation was carried out under aeration of 200 liters of sterile air per minute with 200 rpm stirring. Then, production of bestatin reached the maximum after 48-72 hours.

Bestatin is a stable compound. No decrease of the activity was observed when a culture filtrate containing bestatin was made pH 2.0 or pH 9.0 and heated at 60° C. for 30 minutes.

In culture broth, both the liquid part and the solid part contain bestatin. Bestatin in the solid part, that is, in the mycelium cake, can be extracted with methanol. When the fermentation yield of bestatin is increased, then, the rate of bestatin in the mycelium cake to that in the culture filtrate increases.

Bestatin is a stable compound, therefore, culture filtrate itself can be concentrated by distillation, preferably under reduced pressure, and from the concentrated solution or the dried residue it is extracted with organic solvents such as methanol, ethanol, butanol etc in which bestatin is sufficiently soluble. The cultured beer containing mycelium can be subjected to extraction with a water-immiscible solvent such as propanol, butanol or amylalcohol to extract bestatin in the liquid part and in the mycelium part at one time. When a large amount of culture filtrate is extracted with organic solvent, butanol is preferably used. A counter-current method can be used to purify bestatin. Crude bestatin can then be obtained by concentration under reduced pressure of organic solvent extracts. Usually this crude material contains more than 1% of bestatin. This purity varies according to the amount of bestatin produced in culture filtrate.

Adsorption methods are also useful for extraction and purification of bestatin. For this purpose, active carbon, ion exchange resins, alumina, silica gel, etc. are useful. For instance, bestatin in culture filtrates can be adsorbed by active carbon and, after washing with water, bestatin is eluted with methanol or aqueous methanol. Increased temperature increases the elution yield. For instance, active carbon was added to culture filtrate at 2.0%, the carbon was treated twice with 20 times volume of methanol at 40° C. under stirring, and bestatin was eluted. The yield from the culture filtrate was about 80%. Crude powder of bestatin can be obtained by concentration under reduced pressure of the methanol extract. Chromatography on alumina or silica gel can be utilized for purification of bestatin. Especially, silica gel column chromatography is useful in the final purification step. In this case, n-butanol-acetic acid-water-butyl acetate (4:1:1:6 in volume) is an example used for final purification of bestatin by a silica gel chromatography. Bestatin obtained as described above can be crystallized with a suitable organic solvent such as methanol-benzene. Ion exchange resins are useful in purification of bestatin. Strong and weak cation exchange resins can be used for this purpose.

Properties of bestatin are here described. Bestatin crystallizes as white needle crystals and melts at 233°–236° C. It is optically active, and −30.6° was obtained for $[\alpha]_D^{22}$ in 0.861% methanol solution. The elemental analysis gave the following results: calcd. for $C_{16}H_{24}N_2O_4$: C, 62.32; H, 7.82; N, 9.08; O, 20.75; found C, 60.86; H, 7.79; N, 8.61; O, 21.06. This molecular formula was supported by the mass spectrum. Ultraviolet absorption spectrum of bestatin was observed at a concentration of 500 μg/ml. in methanol.

In the infrared absorption spectrum the following bands are observed: 3400, 3300, 3200, 2920, 2850, 1685, 1635, 1530, 1400, 1315, 1265, 1245, 1175, 1125, 1100, 850, 735, 700 cm$^{-1}$. The nuclear magnetic resonance spectrum of bestatin was taken by Varian HA-100 equipment in tetradeuteromethanol using trimethylsilane as the internal standard and the following signals were observed: 0.9–1.05 (6H), 1.6–1.8 (3H), 2.9–3.15 (2H), 3.6–3.9 (1H), 4.13–4.2 (1H), 4.3–4.55 (1H), 7.35 (5H).

The hydrolysis of bestatin in 6 N HCl at 100° C. for 18 hours yields L-leucine and an unusual amino acid. The ratio of these amino acids is 1:1. Bestatin gives positive Rydon-Smith and ninhydrin reactions. The amino acid sequence of bestatin shown in the structure was elucidated by fragmentation pattern in mass spectrum of bestatin methyl ester hydrochloride. Thus, the structure of bestatin is (2S,3R)-3-amino-2-hydroxy-4-phenylbutyryl-L-leucine.

Based on the carboxyl group, the esters of bestatin can be easily synthesized by treating bestatin with alcohols under usual conditions. Bestatin amide is also synthesized by a usual method. N-acetyl derivatives can be synthesized by treating bestatin with acid anhydride or acid chloride. Bestatin is soluble in acetic acid, pyridine, dimethylsulfoxide, methanol, ethanol and water, less soluble in propanol and butanol, hardly soluble in ethyl acetate, butyl acetate, ethyl ether, hexane, petroleum ether, benzene and chloroform. Equimolecular addition of acid gives acid salt of bestatin which is more soluble in water than bestatin.

In thin layer chromatographies using silica gel G the following Rf values are observed for bestatin in the following solvents: 0.24, butyl acetate-butanol-acetic acid-water (4:4:1:1 in volume); 0.13, butyl acetate-butanol-acetic acid-water (6:4:1:1 in volume).

In high voltage electrophoresis using acidic solvent such as formic acid-acetic acid-water (25:75:900 in volume) under 3500 V for 15 minutes bestatin moves to cathode showing Rm value 0.68 taking L-alanine as 1.0.

Bestatin shows 50% inhibition on aminopeptidase B of rat liver and leucine aminopeptidase of swine kidney at concentrations of 0.055 μg/ml and 0.01 μg/ml respectively. However, bestatin shows only weak inhibition against aminopeptidase A of human serum: 26.4% inhibition at 100 μg/ml. Bestatin was low toxicity and intraperitoneal injection of 295 mg/kg of bestatin causes no toxicity in mouse.

Bestatin also inhibited leucine aminopeptidase. The activity was determined by the following method: to 0.25 ml. of 2 mM L-leucine-3-naphthylamide (Tokyo Chem. Indust. Co., Ltd., Japan) was added 0.5 ml. of 0.1 M Tris-HCl buffer at pH 7.0 and 0.2 ml. of distilled water with or without an inhibitor in a series of test tubes in a 37° C. bath. After 3 minutes, 0.05 ml. of enzyme solution was added and mixed well. Exactly 30 minutes later the reaction was stopped by adding 1.0 ml. of Fast Garnet GBC and measured at 525 nm as described above. The IC$_{50}$ value of bestatin against leucine aminopeptidase was 0.01 μg/ml. Bestatin is competitive with the substrate with a ki value with L-arginine-β-naphthylamide of $6.0 \times 10^{-8}$ M and ki with L-leucine-β-naphthylamide of $2.0 \times 10^{-8}$ M. Bestatin is a specific inhibitor of aminopeptidase B and leucine aminopeptidase. It did not show any inhibition of aminopeptidase A, trypsin, chymotrypsin, elastase, papain, pepsin or thermolysin. Bestatin at 100 μg/ml. showed no antibacterial and no antifungal activities. It has low toxicity with no death after intraperitoneal injection of 300 mg/kg to mice.

Addition of bestatin at 6.25 μg/ml to tissue culture medium increased the activity of bleomycin in inhibiting Yoshida rat sarcoma cells 4–8 times. Simultaneous subcutaneous daily injection of 5 mg/kg of bestatin with 5 mg/kg of bleomycin increased the bleomycin effect on methylcholanthrene-induced squamous cell carcinoma in rats 4 times.

The following examples are described to illustrate this invention; however, our invention should not be limited to the examples. Since the characteristics and the structure of bestatin and the activities of bestatin, its salts and its esters are now clear and bestatin which inhibits aminopeptidase B is widely distributed among actinomycetes, it is easily possible to make various modifications of this invention. In the light of the foregoing disclosure, this invention covers a novel product, bestatin and its acid salt, and processes for production, extraction purification thereof.

EXAMPLE 1

A hundred ml of medium containing 2.0% glucose, 2.0% starch, 2.0% soybean meal, 0.5% yeast extract, 0.25% NaCl, 0.32% CaCO$_3$, 0.0005% CuSO$_4$.5H$_2$O, 0.0005% MnCl$_2$.4H$_2$O and 0.005% ZnSO$_4$.7H$_2$O was placed in a shaking flask of 500 ml volume and sterilized at 120° C. for 20 minutes. PH was adjusted to become 7.0 after the sterilization. One loopful of spores and mycelium of the strain MD976-C7 on the agar medium was inoculated and shake-cultured at 27° C. on a shaking machine (180 rpm/minutes). The pH was 6.5 on the first day of the shaking culture and the same pH was maintained thereafter. The determination of reducing sugar by anthrone method indicated the optical density of 0.855/0.01 ml on the second day, 0.79/0.01 ml on the fifty day. Maximum production of bestatin was attained in 5 days and maintained for 10–12 days thereafter. The cultured broth on the fifty day of 50 shaking flasks were combined and filtered, and adjusted to pH 2.0 with 2 N HCl. The precipitate was removed and the filtrate was extracted with 2400 ml and 2000 ml of n-butanol successively. The butanol extracts were combined and evaporated under reduced pressure, yielding 2.5 g. of crude bestatin as a brown powder. Fifty % inhibition of aminopeptidase B was shown by adding 57 μg of this powder to the test solution.

EXAMPLE 2

The strain MD976-C7 was shake-cultured in the same medium as described in Example 1 for 3 days. One liter of culture beer thus obtained was inoculated into 15 liters of the medium placed in a 30-liter jar fermentor. In this case the medium used for production contained 1.5% maltose, 0.3% yeast extract, 1.0% N-Z amine, 0.3% NaCl. After 2 days at 30° C. under aeration (15 liters/min.) and stirring (250 rpm), 0.04 ml of culture filtrate produced 50% inhibition of aminopeptidase B. The culture broth on the second day of 4 jar fermentors were combined and filtered. The filtrate was passed through a column (4 liters, 10 cm in diameter) of Amberlite XAD-4. After the column was washed with distilled water, bestatin was eluted with 4 liters of methanol. The active eluate was evaporated under reduced pressure. The dried active material was dissolved in 2 liters of distilled water, and after adjusting pH 2.0 this solution was extracted with 2 liters of n-butanol. After washing with distilled water, the butanol solution was evaporated under reduced pressure yielding 30 g. of crude powder. Addition of 21 μg of this powder to the reaction mixture produced 50% inhibition of aminopeptidase B.

EXAMPLE 3

Bestatin was further purified from a crude powder which was obtained as described in Example 2. The powder (30 g.) was dissolved in 3 liters of 0.2 M pyridine-acetic acid buffer pH 3.0 and charged on 500 ml of Dowex 50 X8 (100-200 mesh) equilibrated with 0.2 M pyridine-acetic acid pH 3.0 and washed with 2 liters of the same buffer. Gradient elution was made between 1.0 liter of 0.2 M pyridine-acetic acid (pH 3.0) and 1.0 liter of 1.0 M pyridine-acetic acid (pH 4.75). Active fractions were collected and concentrated under reduced pressure, yielding 2.6 g. of crude bestatin. Addition of 2 μg to the test solution produced 50% inhibition of aminopeptidase B.

EXAMPLE 4

The crude powder prepared by the procedure described in Example 3 was dissolved with 5 ml of methanol and charged on 1.5 liters of Sephadex LH-20 column and eluted with methanol. Active fractions were collected and concentrated under reduced pressure, yielding light yellowish powder of 0.5 g. Addition of 0.4 μg produced 50% inhibition of aminopeptidase B.

EXAMPLE 5

A light yellowish powder prepared by the procedure described in Example 4 was subjected to silica gel column chromatography, using butyl acetate-butanol-acetic acid-water (6:4:1:1). Active fractions were collected and concentrated under reduced pressure. A white powder thus obtained was dissolved in a small amount of methanol and crystallized by adding ethyl acetate dropwise. White needle crystals of bestatin were obtained. Addition of 0.10 μg to the test solution produced 50% inhibition of aminopeptidase B.

EXAMPLE 6

Bestatin (20 mg.) was dissolved in 20 ml. of methanol and 0.5 ml. of conc hydrochloric acid was introduced under stirring for 6 hours at 40° C. This solution was concentrated under reduced pressure and dissolved with a small amount of methanol and subjected to Sephadex LH-20 chromatography using methanol as solvent. Active fractions were collected and concentrated under reduced pressure, yielding white crystals. White crystals thus obtained were dissolved in a small amount of methanol and crystallized by adding ethyl acetate dropwise. White needle crystals (m.p. 213°–216° C.) (15 mg.) of the methyl ester of bestatin were thus obtained and showed 50% inhibition of aminopeptidase B at 8.4 μg. The structure of the methyl ester of bestatin was confirmed by the infrared spectrum and NMR spectrum.

EXAMPLE 7

Acetic anhydride (2 ml.) was added to a solution of bestatin (20 mg.) in methanol (4 ml.), and stirred for two days at room temperature. After the reaction was stopped by adding of distilled water (10 ml.), the reaction mixture was dried in reduced pressure yielding N-acetyl-bestatin methyl ester. This crude N-acetyl-bestatin methyl ester was dissolved in methanol and passed through a column of Sephadex LH-20 to obtain pure N-acetyl-bestatin methyl ester. This structure was ascertained by IR, NMR and mass spectrometry. The pure material inhibited aminopeptidase B ($ID_{50}=8$ μg). The modification of C and/or N-terminal atoms of bestatin reduced the activity of inhibition of aminopeptidase B.

EXAMPLE 8

A medium (300 liters) containing glycerin 2%, polypeptone 1%, yeast extract 0.2%, NaCl 0.3% $K_2HPO_4$ 0.1% $MgSO_4.7H_2O$ 0.1%, $CuSO_4.5H_2O$ 0.0007%, $FeSO_4.7H_2O$ 0.0001%, $MnCl_2.4H_2O$ 0.0008%, $ZnSO_4.7H_2O$ 0.0002%, L-leucine 0.1% L-phenylalanine 0.1%, anti-foaming agent (KM-72) 0.01% was placed stainless steel tank (570 liters) and sterilized at 115° C. for 30 minutes. Culture beer (6 liters) of a strain MD976-C7 shake cultured for 3 days was inoculated and incubated at 29° C. for 96 hours with aeration (300 liters/min) and agitation (230 rpm). The culture broth was filtered, yielding 285 liters of broth filtrate (pH 6.3, $ID_{50}=0.05$ ml), and adjusted to pH 2.8 with HCl. The broth filtrate was extracted with 150 liters of butanol. The butanol extract was concentrated to 98 liters at reduced pressure and washed with water (pH 8.45). The butanol layer was dried in reduced pressure, yielding 101.9 g of bestatin as crude powder ($ID_{50}=26$ μg).

EXAMPLE 9

The crude powder which was obtained as described in Example 8 was purified by the procedure shown in Example 3 and 4. The crude powder of 90.5 g was dissolved in 150 ml of methanol and this solution was chromatographed on Dowex 50 X8 (1500 ml, 100–200 mesh) which was equilibrated with 0.2 M pyridine-acetic acid at pH 3.0. A linear gradient between 3 liters of 1.0 M pyridine-acetic acid (pH 3.0) and 3 liters of 1.0 M pyridine-acetic acid (pH 4.75) was carried out. Active fractions were collected and concentrated under reduced pressure, yielding the bestatin as crude powder (3.89 g.). It showed 50% inhibition of aminopeptidase B at 1.35 μg. For further purification this solution was chromatographed on Sephadex LH-20 (2.6 liters) which was equilibrated with methanol, and eluted with methanol. Active fractions were collected and concentrated under reduced pressure, yielding bestatin as light yellowish powder (1.66 g.). It showed 50% inhibition of aminopeptidase B at 0.52 μg.

EXAMPLE 10

The crude powder which was obtained as described in Example 9 was purified by a procedure similar to that shown in Example 5. The light yellowish powder of 1.66 g was dissolved in 150 ml of methanol and mixed with silica gel. After removed of methanol by evaporation under reduced pressure, the powder was placed on silica gel (5×40 cm) which was equilibrated with butyl acetate-butanol-acetic acid-water (6:4:1:1), and eluted with the same solvent. Active fractions were collected and concentrated under reduced pressure and recrystallized from methanol-ethyl acetate to yield bestatin as white needle crystals (185 mg.). The purified bestatin showed 50% inhibition of aminopeptidase B at 0.1 μg.

Included within the scope of this invention are bestatin, nontoxic, pharmaceutically acceptable acid addition salts of bestatin with inorganic acids and organic acids such as hydrochloric acid, sulfuric acid, acetic acid, succinic acid, etc. and esters of bestatin such as methyl, ethyl, butyl, isobutyl, etc. For therapeutic purpose, salts which are more soluble in water than bestatin are useful and salts and esters which are more insoluble in water than bestatin but more soluble in organic solvents are useful for extraction and purification.

When desired, bestatin and its salts may be admixed with bleomycin to increase the anti-tumor effect of the bleomycin.

The solid resin Amberlite XAD is a macroreticular, crosslinked polystyrene polymer (U.S. Pat. No. 3,531,463). Such macroporous nonionic adsorption resins have an aromatic basic structure with an average pore diameter of 4-20 nm, preferably 7-10 nm, especially polystyrene resins having a surface from 100 to 1,000 m² per gram which are styrene-divinylbenzene copolymers marketed by Rohm & Haas Co. as Amberlite XAD resins.

Dowex 50 is a polystyrene nuclear sulfonic acid resin.

"Sephadex LH-20" is a lypophilic insoluble molecular-sieve chromatographic medium made by cross-linking dextran and marketed by Pharmacia, Uppsala, Sweden. The Sephadex LH-20 used in the preceding examples can be replaced by other similar gel-filtration agents, e.g. Sephadex G25 to G200, Sepharose 4B and 6B (Pharmacia Fine Chemicals AB, Uppsala, Sweden) and Bio-Gel A1.5 m (Bio Rad Co.). Preferred gel-filtration agents include the carboxymethyl substituted cross-linked dextran gels described in columns 3 and 4 of U.S. Pat. No. 3,819,836.

We claim:
1. (2S,3R)-3-amino-2-hydroxy-4-phenylbutanoic acid.

* * * * *